US010302537B2

(12) United States Patent
Xing et al.

(10) Patent No.: US 10,302,537 B2
(45) Date of Patent: May 28, 2019

(54) IMPELLER HIGH-PRECISION STATIC PERFORMANCE SIMULATION DEVICE, TESTING MACHINE AND IMPELLER PERFORMANCE SIMULATION TESTING METHOD

(71) Applicants: Zhiguo Xing, Beijing (CN); Haidou Wang, Beijing (CN); Gang Wang, Beijing (CN)

(72) Inventors: Zhiguo Xing, Beijing (CN); Haidou Wang, Beijing (CN); Gang Wang, Beijing (CN)

( * ) Notice: Subject to any disclaimer, the term of this patent is extended or adjusted under 35 U.S.C. 154(b) by 0 days.

(21) Appl. No.: 15/784,290

(22) Filed: Oct. 16, 2017

(65) Prior Publication Data

US 2018/0106707 A1   Apr. 19, 2018

(30) Foreign Application Priority Data

Oct. 17, 2016 (CN) .......................... 2016 1 0900670
Oct. 17, 2016 (CN) .......................... 2016 1 0902579
Oct. 17, 2016 (CN) .......................... 2016 1 0903074
Oct. 17, 2016 (CN) ..................... 2016 2 1128109 U (51) Int. Cl.
*G01N 3/00* (2006.01)
*G01N 3/16* (2006.01)

(52) U.S. Cl.
CPC ..... *G01N 3/165* (2013.01); *G01N 2203/0037* (2013.01); *G01N 2203/0073* (2013.01)

(58) Field of Classification Search
CPC .......... G01N 3/165; G01N 2203/0037; G01N 2203/0073
USPC ........................................................... 73/826
See application file for complete search history.

(56) References Cited

U.S. PATENT DOCUMENTS

| 5,437,192 | A  | * | 8/1995  | Kawamoto | G01N 33/346 73/159 |
| 6,718,833 | B2 | * | 4/2004  | Xie      | G01N 3/32 73/789   |
| 6,813,960 | B1 | * | 11/2004 | Owen     | G01N 3/32 73/794   |
| 2002/0017144 | A1 | * | 2/2002  | Miles    | G01N 3/32 73/808   |
| 2002/0162400 | A1 | * | 11/2002 | Xie      | G01N 3/32 73/812   |
| 2005/0220428 | A1 | * | 10/2005 | Bottcher | G02B 6/25 385/123  |

* cited by examiner

*Primary Examiner* — Max H Noori
(74) *Attorney, Agent, or Firm* — Parker Highlander PLLC (57) ABSTRACT

An impeller high-precision static performance simulation device, a testing machine, and an impeller performance simulation testing method are provided. In the device, a centrifugal force acting on a blade is simulated by an upper clamper, a lower clamper and a tension sensor. In the process of carrying out a simulation test to the performance of the impeller, a centrifugal force effect of an air compressor impeller is simulated by a static pulling force, to accurately simulate and evaluate the service condition of the impeller under the action of a high-precision static force.

19 Claims, 5 Drawing Sheets

IMPELLER HIGH-PRECISION STATIC PERFORMANCE SIMULATION DEVICE, TESTING MACHINE AND IMPELLER PERFORMANCE SIMULATION TESTING METHOD

CROSS-REFERENCE TO RELATED APPLICATIONS

This application claims priorities to the following four Chinese Patent Applications filed with the Chinese State Intellectual Property Office on Oct. 17, 2016, which are respectively (1) Chinese Patent Application No. 201610900670.8, titled "IMPELLER HIGH-PRECISION STATIC PERFORMANCE SIMULATION DEVICE", (2) Chinese Patent Application No. 201621128109.4, titled "IMPELLER HIGH-PRECISION STATIC PERFORMANCE SIMULATION DEVICE", (3) Chinese Patent Application No. 201610902579.X, titled "TESTING MACHINE", (4) Chinese Patent Application No. 201610903074.5, titled "IMPELLER PERFORMANCE SIMULATION TESTING METHOD", and the entire disclosures of which are incorporated herein by reference.

FIELD

The present application relates to the technical field of testing devices, and more particularly to an impeller high-precision static performance simulation device, a testing machine and an impeller performance simulation testing method.

BACKGROUND

The impeller is an important component of an air compressor, and is an important part that ensures the performance, reliability and durability of the air compressor.

In the working process of the air compressor, a blade rotating at a high speed may be subjected to a great centrifugal force, and thus defects such as micro-cracks are apt to be generated on the surface and inside of the blade. Accordingly, the service performance of a blade under the action of the centrifugal force is of great significance to the durability and reliability of the impeller in service.

An impeller performance test in the remanufacturing or production process of impellers has a guiding significance for the subsequent mass production of impellers. Therefore, it becomes a technical issue to be addressed urgently by the person skilled in the art to simulate the effect of a centrifugal force of an impeller of an air compressor so as to accurately simulate and evaluate the service performance of the impeller under the action of a high-precision static force.

SUMMARY

In view of this, an impeller high-precision static performance simulation device, a testing machine and an impeller performance simulation testing method are provided according to the present application, so as to simulate the effect of a centrifugal force of an impeller of an air compressor and accurately simulate and evaluate the service performance of the impeller under the action of a high-precision static force. Moreover, the testing machine and the impeller performance simulation testing method can address the issues of poor simulation effect and low simulation efficiency in performing simulation to blades in the conventional technology.

The following technical solutions are provided according to the present application.

An impeller high-precision static performance simulation device includes a frame and an upper clamper and a lower clamper arranged on the frame. The upper clamper and the lower clamper are respectively configured to clamp two ends of a blade and apply a set tension to the blade to simulate a centrifugal force acting on the blade, and the upper clamper is provided with a tension sensor.

A testing machine configured to test a blade of an air compressor includes:
  a frame;
  an upper clamper and a lower clamper arranged on the frame, wherein the upper clamper and the lower clamper are respectively configured to clamp two ends of the blade and apply a set tension to the blade to simulate a centrifugal force acting on the blade, and the upper clamper is provided with a tension sensor;
  a test chamber arranged on a mounting table of the frame, and configured to cover the blade; and
  an air supplier arranged on the frame and in communication with the test chamber and configured to supply air into the test chamber to simulate a load generated by a fluid medium on the blade.

Preferably, in the testing machine, the air supplier includes a blower and a ventilation duct, and the ventilation duct has one end connected to an air outlet of the blower and another end in communication with the test chamber.

Preferably, the testing machine further includes an air pressure adjuster, the air pressure adjuster includes a servo motor and a frequency conversion device connected to the servo motor. The frequency conversion device includes: a valve body arranged on the ventilation duct, a valve seat arranged in the valve body, and a valve core fitted with the valve seat. The valve core is connected to the servo motor via a connecting shaft; the servo motor drives the valve core to rotate with respect to the valve seat via the connecting shaft to switch the valve body between a closed state and an open state.

Preferably, in the testing machine, the lower clamper includes: a clamper base arranged on the mounting table, and two clamping blocks arranged on the clamper base and symmetrically distributed. The two clamping blocks are fixed to the clamper base by means of a bolt assembly, and a holding chamber configured to hold a bottom end of the blade is formed between the two clamping blocks.

Preferably, the testing machine further includes: a worm and worm wheel mechanism, and a drive gear meshed with the clamper base. The drive gear is arranged on an output shaft of the worm and worm wheel mechanism, the worm and worm wheel mechanism is provided with a drive handle, and the worm and worm wheel mechanism is configured to drive the clamper base to rotate via the drive gear to adjust an orientation of the holding chamber.

Preferably, in the testing machine, the frame includes an electric cylinder and a right-angled lever. The electric cylinder is arranged at the bottom of the right-angled lever, the upper clamper is arranged at the top of the right-angled lever, and the electric cylinder is capable of urging the right-angled lever to allow the upper clamper to clamp a top end of the blade.

Preferably, in the testing machine, a top end of the right-angled lever is provided with a lifter, and the lifter is capable of raising and lowering relative to the top end of the right-angled lever to adjust a distance between the upper clamper and the lower clamper.

Preferably, in the testing machine, the electric cylinder is a GSX Series electric cylinder Preferably, the testing machine further includes a controller. The controller is connected to both the tension sensor and the lifter, and the controller is configured to control the lifter to raise till a value detected by the tension sensor reaches a set value.

Preferably, the testing machine further includes a swinging system. The swinging system is arranged on the frame and is configured to be connected to the blade to drive the blade to swing.

An impeller performance simulation testing method for detecting a blade of an air compressor includes:

clamping, by an upper clamper and a lower clamper provided on the frame, two ends of the blade respectively to locate the blade between the upper clamper and the lower clamper, and applying a set tension to the blade to simulate a centrifugal force acting on the blade;

supplying, by an air supplier, air into a test chamber covering the blade, to simulate the application of a load generated by a fluid medium on the blade; and establishing a static mechanical model of the blade under the action of the centrifugal force.

Preferably, in the impeller performance simulation testing method, the upper clamper is provided with a tension sensor configured to test the magnitude of the tension.

Preferably, the impeller performance simulation testing method further includes performing, by an air pressure adjuster, frequency conversion to the air pressure, to allow the blade to generate a slight vibration at a predetermined frequency. The air pressure adjuster includes a servo motor and a frequency conversion device connected to the servo motor.

In the device according to the present application, a centrifugal force acting on the blade is simulated by an upper clamper, a lower clamper and a tension sensor. In the process of carrying out a simulation test to the performance of the impeller, a centrifugal force effect the impeller of an air compressor is simulated by a static pulling force, to accurately simulate and evaluate the service condition of the impeller under the action of a high-precision static force.

BRIEF DESCRIPTION OF THE DRAWINGS

For more clearly illustrating embodiments of the present application or technical solutions in the conventional technology, drawings used in the description of the embodiments or the conventional technology will be briefly described hereinafter. Obviously, the drawings in the following description are merely some embodiments of the present application, and for the person skilled in the art, other drawings may be obtained based on these drawings without any creative efforts.

DETAILED DESCRIPTION

The present application is described in further detail hereinafter with reference to the drawings for enabling the person skilled in the art to better understand the technical solutions of the present application.

Figure 1:
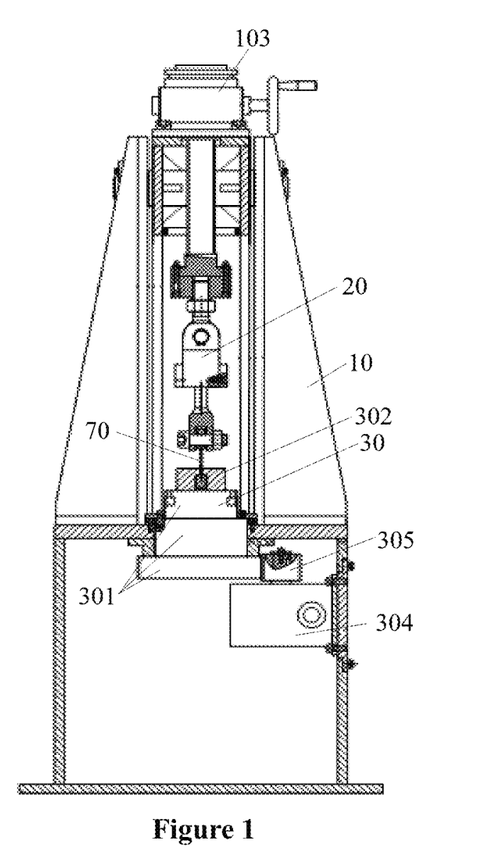
FIG. 1 is a front view of a testing machine according to an embodiment of the present application, with a test chamber not shown in the drawing.
Figure 2:
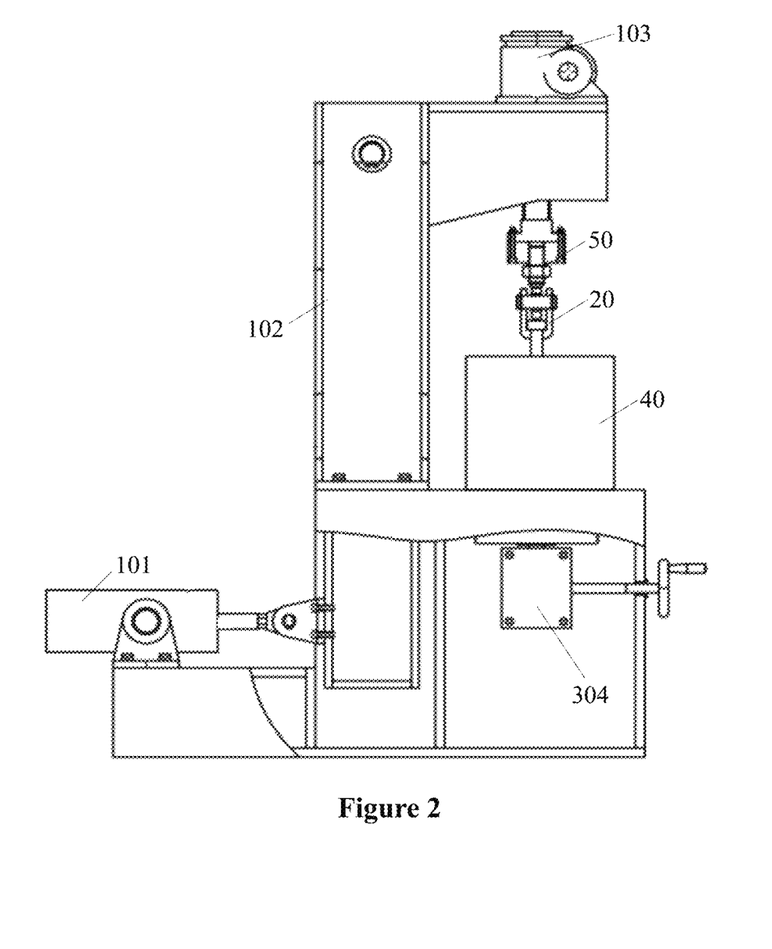
FIG. 2 is a side view of FIG. 1, with the test chamber shown.

Referring to FIGS. 1 and 2, an impeller high-precision static performance simulation device is provided according to an embodiment of the present application, which, in the process of carrying out a simulation test to the performance of an impeller, simulates the effect of a centrifugal force of the impeller of an air compressor by applying a static tension to accurately simulate and evaluate the service situation of an impeller under the action of a high-precision static force.

The impeller high-precision static performance simulation device shown in FIGS. 1 and 2 includes a frame 10, an upper clamper 20, a lower clamper 30, a test chamber 40, and a tension sensor 50.

The frame 10, as a framework for the entire impeller high-precision static performance simulation device, is configured to provide a mounting base for other parts and components. The upper clamper 20 and the lower clamper 30 are arranged on the frame 10. Generally, the upper clamper 20 is arranged at a top end of the frame 10 and the lower clamper 30 is arranged on a mounting table of the frame 10, and the mounting table can also be regarded as a working table of the whole impeller high-precision static performance simulation device. The upper clamper 20 and the lower clamper 30 are respectively configured to clamp two ends of a blade 70, which are respectively a top end and a bottom end of the blade 70. The upper clamper 20 and the lower clamper 30 respectively apply a set tension to the blade 70 to simulate a centrifugal force acting on the blade 70. In order to ensure that the applied tension can more accurately simulate the centrifugal force acting on the blade 70 under working condition, the upper clamper 20 is provided with a tension sensor 50. The tension sensor 50 is configured to show a tension applied to the blade 70, and when the tension is insufficient, the tension sensor 50 may serve the function of reminding of subsequent re-adjustment.

Referring to FIGS. 1 and 2, a testing machine is provided according to an embodiment of the present application, and is configured to perform an experimental test to the blade of an impeller of an air compressor to simulate the effect of a centrifugal force of the impeller of the air compressor so as to accurately simulate and evaluate the service performance of the impeller under the action of a high-precision static force, and address the issues of poor simulation effect and low simulation efficiency existing presently in performing simulation to blades of the air compressor impeller.

The testing machine shown in FIGS. 1 and 2 includes a frame 10, an upper clamper 20, a lower clamper 30, a test chamber 40, a tension sensor 50 and an air supplier 60.

The frame 10, as a framework for the entire impeller high-precision static performance simulation device, is configured to provide a mounting base for other parts and components. The upper clamper 20 and the lower clamper 30 are arranged on the frame 10. Generally, the upper clamper 20 is arranged at a top end of the frame 10 and the lower clamper 30 is arranged on a mounting table of the frame 10, and the mounting table can also be regarded as a working table of the whole impeller high-precision static performance simulation device. The upper clamper 20 and the lower clamper 30 are respectively configured to clamp two ends of a blade 70, which are respectively a top end and a bottom end of the blade 70. The upper clamper 20 and the lower clamper 30 respectively apply a set tension to the blade 70 to simulate a centrifugal force applied on the blade 70. In order to ensure that the applied tension can more accurately simulate the centrifugal force applied on the blade 70 under working condition, the upper clamper 20 is provided with a tension sensor 50. The tension sensor 50 is configured to show a tension applied to the blade 70, and when the tension is insufficient, the tension sensor 50 may serve the function of reminding of subsequent re-adjustment.

The test chamber 40 is arranged on the mounting table of the frame 10, and is configured to cover the blade 70 to provide a relatively closed simulation environment. The air supplier 60 is arranged on the frame 10 and is in communication with the test chamber 40. The air supplier 60 supplies air into the test chamber 40, to allow the airflow to act on the blade 70 in the test chamber 40, thus finally achieving the object of simulating the load generated by a flowing medium and subjected by the blade 70 in working condition.

It is known that the centrifugal force applied on the blade 70 of the impeller in a high-speed rotation state is characterized as follows: the centrifugal force is constant, and has a certain direction, i.e., an outward direction along the radius of rotation. Based on this, a high-precision static force, i.e., a static tension, is adopted in the present application to simulate a centrifugal force applied on the blade 70. In the simulation process, the static force acting on the blade 70 is a tension applied by the upper clamper 20 and the lower clamper 30 to the blade 70. Specifically, the static force can be adjusted by adjusting a clamping distance between the upper clamper 20 and the lower clamper 30, and can also be adjusted by adjusting the position of the upper clamper 20 relative to the lower clamper 30. As described above, in the above-described adjustment processes, the adjustment can be realized with the cooperation of the tension sensor 50.

The air supplier 60 blows air into the test chamber 40 and applies an action force to the blade in the test chamber 40 to simulate the stress condition of the blade 70 when operating in a chamber of the air compressor.

According to the above description, the testing machine according to the embodiment of the present application is capable of simulating both the load applied by a fluid medium on the blade 70 by means of the air supplier 60 and the test chamber 40, and the centrifugal force applied on the blade by means of the upper clamper 20, the lower clamper 30 and the tension sensor 50. In the process of performing the simulation test to the performance of the blade, the testing machine according to this embodiment can simultaneously perform both simulations as described above to the blade, thus may improve the simulation efficiency. Moreover, the simulation test of two kinds of stress conditions to the blade can accord with the real stress condition of the blade, and thus can improve the test effect.

Figure 3:
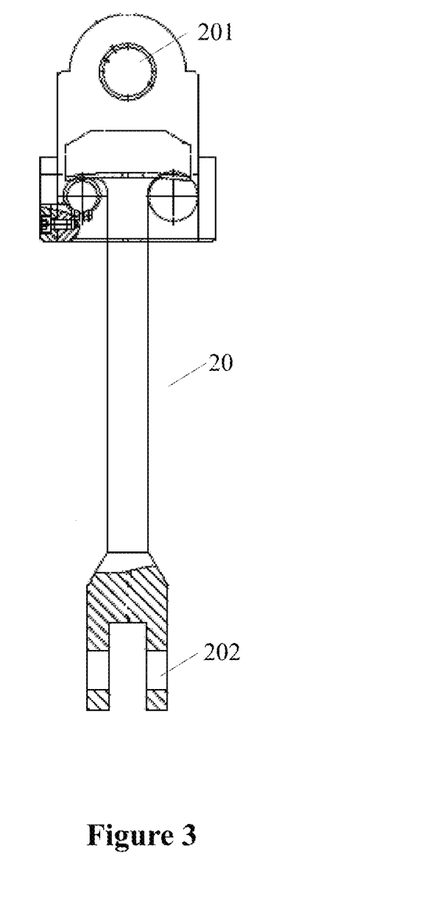
FIG. 3 is a schematic view showing the structure of an upper clamper according to an embodiment of the present application.
Figure 4:
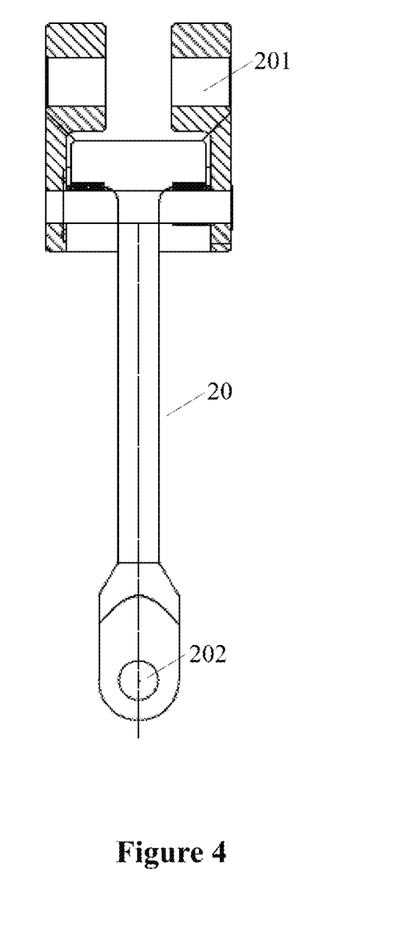
FIG. 4 is a side view of FIG. 3.

In this embodiment, the upper clamper 20 and the lower clamper 30 function to clamp the top end and the bottom end of the blade 70, and there are various types of clamping devices for realizing the above-described function. Referring to FIGS. 3 and 4, an upper clamper 20 having a specific structure is provided according to an embodiment of the present application, and the upper clamper 20 provided has an integral structure with a top hinge hole 201 provided at the top and a bottom hinge hole 202 provided at the bottom. The top hinge hole 201 is hinged to the top end of the frame 10 by means of a hinge shaft, and the bottom hinge hole 202 is hinged to the top end of the blade 70 by means of a hinge shaft. The above hinge manner allows the blade 70 to swing slightly under the action of the load generated by the fluid medium, thus can simulate the swing of the blade 70 generated while working more accurately, and further can simulate the stress condition of the blade 70 better. Specifically, the testing machine according to this embodiment may further include a swinging system which is connected to the blade 70 and is capable of actively driving the blade 70 to swing within an appropriate angle range.

Figure 5:
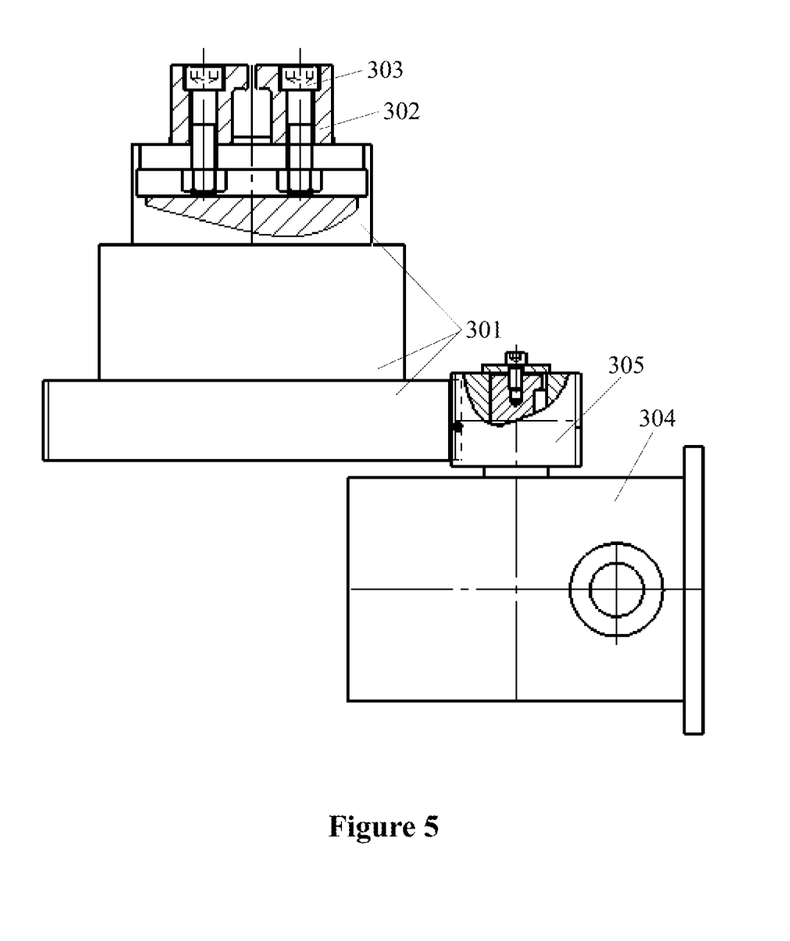
FIG. 5 is a schematic view showing the structure of a lower clamper according to an embodiment of the present application.

Similarly, a lower clamper 30 having a specific structure is provided according to an embodiment of the present application. Referring to FIG. 5, the lower clamper 30 provided includes a clamper base 301, two clamping blocks 302 and a bolt assembly 303. The clamper base 301 is arranged on the mounting table. The two clamping blocks 302 are arranged symmetrically on the clamper base 301 and are secured to the clamper base 301 by means of the bolt assembly 303. A holding chamber configured to hold the bottom end of the blade 70 is formed between the two clamping blocks 302. Specifically, the two clamping blocks 302 are movably arranged on the clamper base 301 and then are fixed by the bolt assembly 303. The movement of the two clamping blocks 302 can change the width of the holding chamber and thus the holding chamber can be adapted to the blades 70 of different specifications.

Referring again to FIG. 5, the testing machine according to this embodiment may further include a worm and worm wheel mechanism 304 and a drive gear 305. The drive gear 305 is engaged with the clamper base 301, that is, meshing teeth are provided in the circumferential direction of the clamper base 301, and the drive gear 305 is rotatable with respect to the clamper base 301. The drive gear 305 is arranged on an output shaft of the worm and worm wheel mechanism 304. The worm and worm wheel mechanism 304 is provided with a drive handle, and the drive handle is operated to drive the worm and worm wheel mechanism 304 to further achieve the rotation of the drive gear 305. The rotation of the drive gear 305 can drive the clamper base 301 to rotate, to finally achieve the object of adjusting the orientation of the holding chamber. The worm and worm wheel mechanism 304 is driven by the drive handle to adjust the angle of the lower clamper 30, thus the control is simple and convenient. Moreover, the worm and worm wheel mechanism 304 has a self-locking effect, which can ensure the testing position of the blade 70. A rotary surface of the clamper base 301 may be provided with thin oil grooves for lubrication, so that the friction force of the contact surface is reduced and the angle adjustment is easy.

Referring again to FIGS. 1 and 2, in this embodiment, a frame 10 having a specific structure is provided according to this embodiment. The frame 10 includes an electric cylinder 101 and a right-angled lever 102. The electric cylinder 101 is arranged at the bottom of the right-angled lever 102, and the upper clamper 20 is provided at the top of the right-angled lever 102. The electric cylinder 101 may urge the right-angled lever 102 to swing to adjust and indirectly pull the upper clamper 20 to achieve the objects of clamping the top end of the blade 70 and applying the tension. The right-angled lever 102 can function to adjust the angle and position of the upper clamper 20, and moreover, by appropriately arranging the fulcrum of the right-angled lever 102, the right-angled lever 102 is enabled to enlarge the thrust of the electric cylinder 101 and also change a thrust direction of the electric cylinder 101. Considering that the right-angled lever 102 is subjected to a large force, in order to meet a high strength light weight requirement, the structure of the right-angled lever 102 is designed to be a welding member and appropriate rib plate and reinforcing plate are designed to increase the overall strength of the right-angled lever 102. In this embodiment, the frame 10 can achieve an accurate loading of a static force by the high-precision loading of the electric servo system (electric cylinder) and the right-angled lever 102.

In the present application, the electric cylinder 101 serves as a power source, and may be embodied as an imported GSX Series electric cylinder. The electric cylinder of such series has a planetary roller screw rod organically combined with a motor rotor, where the planetary rollers are uniformly mounted around the main screw rod, and then the planetary roller screw rod is precisely mounted into a hollow rotor, thus ensuring the planetary roller screw rod to be absolutely synchronous with the rotor. The electric cylinder of such series employs a T-LAM segmented lamination stator technology, which can continuously output a torque higher than that outputted by a conventional motor, and has an independent coil winding. The segmented stator combination ensures a highest performance of the motor, and can improve the effect of the motor, and also can further effectively reduce the heat effect generated by the coils of the motor and eliminate the rotation of the end of the stator. A thermal conductive ceramic is utilized to replace components and parts of a conventional motor to improve the reliability. Moreover, the electric cylinder 101 in the advanced closed-loop servo system can accurately control the speed, thrust and position, with a control accuracy reaching 0.02 mm.

Referring again to FIGS. 1 and 2, in this embodiment, the top end of the right-angled lever 102 may be provided with a lifter 103. The lifter 103 can be raised and lowered relative to the top end of the right-angled lever 102 to adjust the distance between the upper clamper 20 and the lower clamper 30, and further indirectly adjust the tensions applied to the blade 70 by the upper clamper 20 and the lower clamper 30. Specifically, the lifter 103 may be embodied as a worm wheel and screw rod type lifting machine, which can facilitate the clamping of the blade 70, and has advantages such as a compact structure, a light weight, having no noise, a high carrying capacity, being self-locking, having an anti-rotated pushrod, a high reliability and a long service life. Moreover, the raising and lowering movements of the lifter 103 can help adjust the leveling of the right-angled lever 102 and ensure a vertically upward load.

The testing machine according to this embodiment may further include a controller connected to both the tension sensor 50 and the lifter 103. The controller is configured to control the lifter 103 to move upward till a value detected by the tension sensor 50 reaches a set value. Specifically, the controller may control the start and stop of the lifter 103 based on the comparison result of a real-time tension value detected by the tension sensor 50 and the set value. The PID control method can better ensure a high precise loading of the static force.

Figure 6:
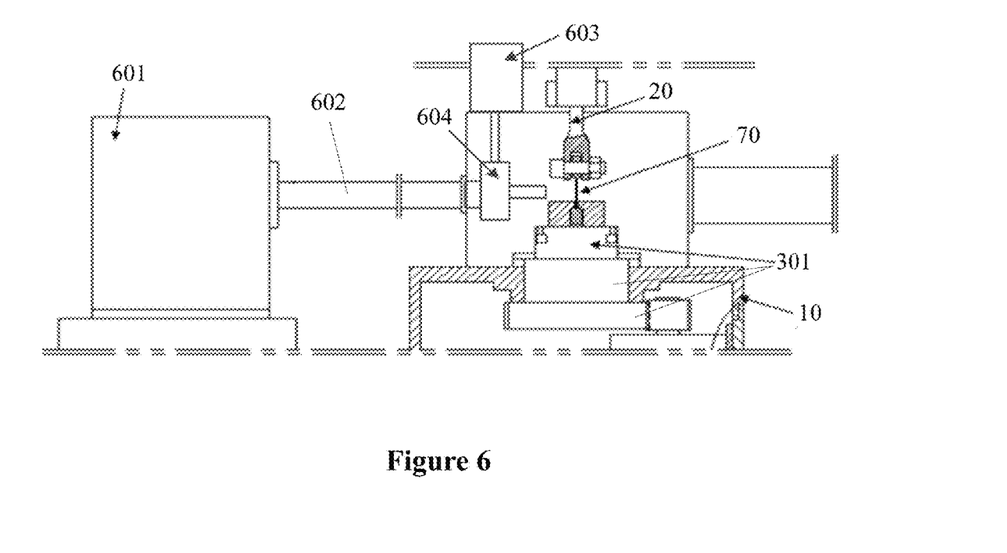
FIG. 6 is a partially enlarged schematic view of a testing machine according to an embodiment of the present application.
Figure 7:
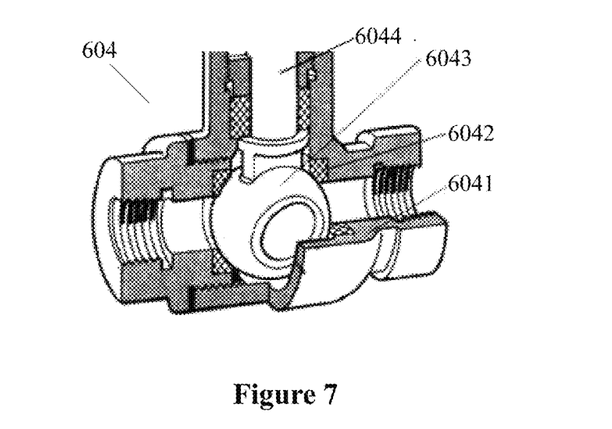
FIG. 7 is a schematic view showing an internal structure of a frequency conversion device according to an embodiment of the present application.

Referring to FIG. 6, in the testing machine according to an embodiment of the present application, the air supplier 60 includes a blower 601 and a ventilation duct 602. The ventilation duct 602 has one end connected to an air outlet of the blower 601 and another end connected to the test chamber 40, thus achieving the purpose of blowing air into the test chamber 40. Reference may be made to FIG. 7, the air supplier 60 provided may further include a servo motor 603 and a frequency conversion device 604 connected to the servo motor 603. The frequency conversion device 604 includes a valve body 6041, a valve seat 6042, a valve core 6043 and a connecting shaft 6044. The valve body 6041 is arranged on the ventilation duct 602, the valve seat 6042 is arranged within the valve body 6041, the valve core 6043 matches with the valve seat 6042, the valve body 6041 is connected to the servo motor 603 by the connecting shaft 6044, and the servo motor 603 drives the valve core 6043 via the connecting shaft 6044 to rotate with respect to the valve seat 6042 to achieve the switching of the valve body 6041 between an open state and a closed state, thus finally achieving the open and close of the ventilation duct 602. Of course, variation of a rotating angle of the valve core 6043 may adjust the opening of the valve body 6041, to achieve a more precise control of air amount.

An impeller performance simulation testing method is provided according to the present application to detect a blade of an air compressor, and includes:

clamping, by an upper clamper and a lower clamper provided on a frame, two ends of the blade respectively to locate the blade between the upper clamper and the lower clamper, and applying a set tension to the blade to simulate a centrifugal force acting on the blade;

supplying, by an air supplier, air into a test chamber covering on the blade to simulate a load generated by a fluid medium to the blade; and establishing a static mechanical model of the blade under the action of the centrifugal force.

With the impeller performance simulation testing method according to the present application, the load applied by the fluid medium on the blade can be simulated through the air supplier and the test chamber, and the centrifugal force acting on the blade can be simulated by means of the upper clamper, the lower clamper and the tension sensor, and a static mechanical model of the impeller under the action of the centrifugal force is established, thus the service situation of the impeller under the action of a high-precision static force can be accurately simulated and evaluated.

The impeller performance simulation testing method according to the present application can be implemented by operating on the above-described testing machine.

The exemplary embodiments of the present application have been described by way of illustration only, and undoubtedly, for the person skilled in the art, the embodiments described can be modified in various manners without departing from the spirit and scope of the present application. Accordingly, the foregoing drawings and description are illustrative in nature and should not be construed as limiting the scope of the present application as defined by the appended claims.

The invention claimed is:

1. A testing machine configured to test a blade of an air compressor, comprising:
a frame;
an upper clamper and a lower clamper arranged on the frame, wherein the upper clamper and the lower clamper are respectively configured to clamp two ends of the blade and apply a set tension to the blade to simulate a centrifugal force acting on the blade, and the upper clamper is provided with a tension sensor;
a test chamber arranged on a mounting table of the frame, and configured to cover the blade; and
an air supplier, which is arranged on the frame, and is in communication with the test chamber and configured to supply air into the test chamber to simulate a load generated by a fluid medium.

2. The testing machine according to claim 1, wherein the air supplier comprises a blower and a ventilation duct, and the ventilation duct has one end connected to an air outlet of the blower and another end in communication with the test chamber.

3. The testing machine according to claim 2, further comprising an air pressure adjuster, wherein the air pressure adjuster comprises a servo motor and a frequency conversion device connected to the servo motor, and the frequency conversion device comprises:
   a valve body arranged on the ventilation duct,
   a valve seat arranged in the valve body, and
   a valve core matching with the valve seat, wherein
   the valve core is connected to the servo motor via a connecting shaft, the servo motor drives the valve core to rotate with respect to the valve seat via the connecting shaft in order to switch the valve body between a closed state and an open state.

4. The testing machine according to claim 1, wherein the lower clamper comprises:
   a clamper base arranged on the mounting table; and
   two clamping blocks arranged on the clamper base and symmetrically distributed;
   wherein
   the two clamping blocks are fixed to the clamper base by means of a bolt assembly, and a holding chamber configured to clamp a bottom end of the blade is formed between the two clamping blocks.

5. The testing machine according to claim 4, further comprising:
   a worm and worm wheel mechanism; and
   a drive gear engaged with the clamper base, wherein
   the drive gear is arranged on an output shaft of the worm and worm wheel mechanism, the worm and worm wheel mechanism is provided with a drive handle, and the worm and worm wheel mechanism is configured to drive the clamper base to rotate via the drive gear to adjust an orientation of the holding chamber.

6. The testing machine according to claim 1, wherein the frame comprises an electric cylinder and a right-angled lever, wherein:
   the electric cylinder is arranged at the bottom of the right-angled lever;
   the upper clamper is arranged at the top of the right-angled lever, and the electric cylinder is capable of urging the right-angled lever to allow the upper clamper to clamp a top end of the blade.

7. The testing machine according to claim 6, wherein a top end of the right-angled lever is provided with a lifter, and the lifter is capable of raising and lowering relative to the top end of the right-angled lever to adjust a distance between the upper clamper and the lower clamper.

8. The testing machine according to claim 7, wherein the electric cylinder is a GSX Series electric cylinder.

9. The testing machine according to claim 7, further comprising a controller, wherein the controller is connected to both the tension sensor and the lifter, and the controller is configured to control the lifter to raise till a value detected by the tension sensor reaches a set value.

10. The testing machine according to claim 1, further comprising a swinging system, wherein the swinging system is arranged on the frame and is configured to be connected to the blade to drive the blade to swing.

11. The testing machine according to claim 2, further comprising a swinging system, wherein the swinging system is arranged on the frame and is configured to be connected to the blade to drive the blade to swing.

12. The testing machine according to claim 3, further comprising a swinging system, wherein the swinging system is arranged on the frame and is configured to be connected to the blade to drive the blade to swing.

13. The testing machine according to claim 4, further comprising a swinging system, wherein the swinging system is arranged on the frame and is configured to be connected to the blade to drive the blade to swing.

14. The testing machine according to claim 5, further comprising a swinging system, wherein the swinging system is arranged on the frame and is configured to be connected to the blade to drive the blade to swing.

15. The testing machine according to claim 6, further comprising a swinging system, wherein the swinging system is arranged on the frame and is configured to be connected to the blade to drive the blade to swing.

16. The testing machine according to claim 7, further comprising a swinging system, wherein the swinging system is arranged on the frame and is configured to be connected to the blade to drive the blade to swing.

17. An impeller performance simulation testing method for detecting a blade of an air compressor, comprising:
   clamping, by an upper clamper and a lower clamper provided on the frame, two ends of the blade respectively to locate the blade between the upper clamper and the lower clamper, and applying a set tension to the blade to simulate a centrifugal force acting on the blade;
   supplying, by an air supplier, air into a test chamber covering the blade to simulate a load applied by a fluid medium on the blade; and
   establishing a static mechanical model of the blade under the action of the centrifugal force.

18. The impeller performance simulation testing method according to claim 17, wherein the upper clamper is provided with a tension sensor configured to test the magnitude of the tension.

19. The impeller performance simulation testing method according to claim 18, further comprising:
   performing, by an air pressure adjuster, frequency conversion to the air pressure to allow the blade to generate a slight vibration with a predetermined frequency, wherein
   the air pressure adjuster comprises a servo motor and a frequency conversion device connected to the servo motor.

* * * * *